(12) United States Patent
Soh et al.

(10) Patent No.: US 12,378,345 B2
(45) Date of Patent: Aug. 5, 2025

(54) POLYFUNCTIONAL VINYL RESIN AND METHOD FOR PRODUCING SAME, POLYFUNCTIONAL VINYL RESIN COMPOSITION, CURED ARTICLE, PREPREG, RESIN SHEET, AND LAMINATED PLATE

(71) Applicants: NIPPON STEEL Chemical & Material Co., Ltd., Tokyo (JP); KUKDO CHEMICAL CO., LTD., Seoul (KR)

(72) Inventors: Masahiro Soh, Tokyo (JP); Kazuo Ishihara, Tokyo (JP); Jaeman Han, Seoul (KR); Haerry Youn, Seoul (KR)

(73) Assignees: NIPPON STEEL Chemical & Material Co., Ltd., Tokyo (JP); KUKDO CHEMICAL CO., LTD., Seoul (KR)

( * ) Notice: Subject to any disclaimer, the term of this patent is extended or adjusted under 35 U.S.C. 154(b) by 407 days.

(21) Appl. No.: 17/926,131

(22) PCT Filed: May 13, 2021

(86) PCT No.: PCT/JP2021/018295
§ 371 (c)(1),
(2) Date: Nov. 18, 2022

(87) PCT Pub. No.: WO2021/241255
PCT Pub. Date: Dec. 2, 2021

(65) Prior Publication Data
US 2023/0183409 A1    Jun. 15, 2023

(30) Foreign Application Priority Data
May 28, 2020  (JP) .................... 2020-093240

(51) Int. Cl.
C08F 283/00    (2006.01)
B32B 27/12    (2006.01)
(Continued)

(52) U.S. Cl.
CPC ............ *C08F 283/00* (2013.01); *B32B 27/12* (2013.01); *B32B 27/18* (2013.01); *B32B 27/30* (2013.01);
(Continued)

(58) Field of Classification Search
CPC ........ C08G 61/02; C08F 283/00; C08F 12/32; C08F 299/02; C08J 5/24; C07C 41/14; C07C 43/205; D06M 13/152; D06M 17/06
See application file for complete search history.

(56) References Cited

U.S. PATENT DOCUMENTS 4,692,485 A * 9/1987 Leistner .................. C08F 12/32
526/263
4,707,558 A  11/1987 Wang et al.
(Continued)

FOREIGN PATENT DOCUMENTS

CN  109305896  2/2019
JP  S6368537  3/1988
(Continued)

OTHER PUBLICATIONS

"International Search Report (Form PCT/ISA/210) of PCT/JP2021/018295," mailed on Aug. 3, 2021, with English translation thereof, pp. 1-6.
(Continued)

*Primary Examiner* — Larissa Rowe Emrich
(74) *Attorney, Agent, or Firm* — JCIPRNET

(57) ABSTRACT

Provided is a resin material showing a high thermal conductivity and having high heat resistance while having a low
(Continued)

dielectric constant and a low dielectric loss tangent. The material is a polyfunctional vinyl resin, which is represented by the following general formula (1):

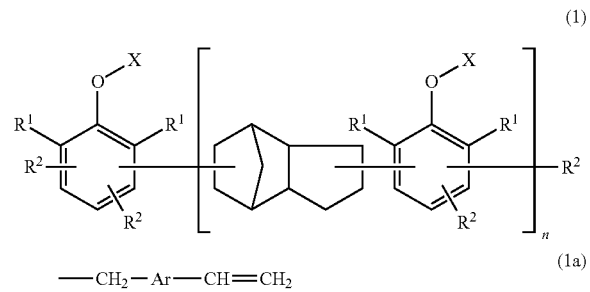

(1)

$$-CH_2-Ar-CH=CH_2 \quad (1a)$$

where $R^1$s each independently represent a hydrocarbon group having 1 to 8 carbon atoms, $R^2$s each independently represent a hydrogen atom or a dicyclopentenyl group, and at least one thereof represents a dicyclopentenyl group, Xs each independently represent a hydrogen atom or a vinyl group-containing aromatic group represented by the formula (1a), and at least one thereof represents a vinyl group-containing aromatic group, "n" represents a number of repetitions, and the average thereof is a number of from 1 to 5, and Ar represents an aromatic ring.

11 Claims, 2 Drawing Sheets

(51) Int. Cl.
| | | |
|---|---|---|
| B32B 27/18 | (2006.01) | |
| B32B 27/30 | (2006.01) | |
| C08G 61/02 | (2006.01) | |
| C08J 5/24 | (2006.01) | |
| B32B 5/02 | (2006.01) | |

(52) U.S. Cl.
CPC ............... *C08G 61/02* (2013.01); *C08J 5/24* (2013.01); *B32B 5/022* (2013.01); *B32B 5/024* (2013.01); *B32B 2260/021* (2013.01); *B32B 2260/046* (2013.01); *B32B 2262/0223* (2013.01); *B32B 2262/0246* (2013.01); *B32B 2262/0269* (2013.01); *B32B 2262/0276* (2013.01); *B32B 2262/062* (2013.01); *B32B 2262/065* (2013.01); *B32B 2262/101* (2013.01); *B32B 2262/103* (2013.01); *B32B 2262/106* (2013.01); *B32B 2307/204* (2013.01); *B32B 2307/302* (2013.01); *C08J 2351/08* (2013.01)

(56) References Cited

U.S. PATENT DOCUMENTS

| 4,728,708 A | | 3/1988 | Zupancic et al. |
| 5,344,899 A | * | 9/1994 | Enomoto ............... C08G 61/02 |
| | | | 525/534 |
| 2007/0213499 A1 | | 9/2007 | Jera et al. |

FOREIGN PATENT DOCUMENTS

| JP | S6465110 | 3/1989 |
| JP | 101503238 | 11/1989 |
| JP | H10931006 | 2/1997 |
| JP | 2003306591 | 10/2003 |
| JP | 2004323730 | 11/2004 |
| JP | 2007308685 | 11/2007 |

OTHER PUBLICATIONS

Z. K. Liao et al., "The synthesis and characterization of novel thermosettable vinylbenzyl terminated monomers and the properties of the cured resins", Polymer Bulletin, vol. 22, Issue 1, Jul. 1989, pp. 1-7.

* cited by examiner

POLYFUNCTIONAL VINYL RESIN AND METHOD FOR PRODUCING SAME, POLYFUNCTIONAL VINYL RESIN COMPOSITION, CURED ARTICLE, PREPREG, RESIN SHEET, AND LAMINATED PLATE

CROSS-REFERENCE TO RELATED APPLICATION

This application is a 371 application of the International PCT application serial no. PCT/JP2021/018295, filed on May 13, 2021, which claims the priority benefits of Japan Patent Application No. 2020-093240, filed on May 28, 2020. The entirety of each of the above-mentioned patent applications is hereby incorporated by reference herein and made a part of this specification.

TECHNICAL FIELD

The present invention relates to a polyfunctional vinyl resin and a polyfunctional vinyl resin composition each having both of a low dielectric loss tangent and a high thermal conductivity, which are useful for a printed board, a sealing material, a casting material, and the like for an electronic device, and cured articles thereof.

BACKGROUND ART

Along with an increase in amount of information communication in recent years, information communication in a high frequency band has started to be actively carried out. Accordingly, there has been a demand for an electrically insulating material having more excellent electrical characteristics, in particular, a low dielectric constant and a low dielectric loss tangent for reducing a transmission loss in the high frequency band, especially small changes in dielectric characteristics after severe thermal history. Further, a printed board or an electronic part using such electrically insulating material is exposed to a high-temperature solder reflow at the time of its mounting, and hence a material showing high heat resistance, that is, a high glass transition temperature has been desired. In particular, recently, in view of environmental problems, lead-free solder having a high melting point has been used, and hence there has been a growing demand for an electrically insulating material having higher heat resistance. To cope with such demand, cured resins using vinyl benzyl ether resins having various chemical structures have heretofore been proposed.

For example, a cured resin, such as a divinyl benzyl ether resin of a bisphenol or a phenol novolac-type polyvinyl benzyl ether resin, has been proposed as such cured resin (Patent Literature 1 and Patent Literature 2). However, those vinyl benzyl ether resins have not provided sufficient characteristics in terms of initial dielectric characteristics. Moreover, the resins have been unable to provide cured resins that always show small changes in dielectric characteristics against severe thermal history, and hence it has been unable to say that the resins each have sufficiently high heat resistance.

Several vinyl benzyl ether resins having specific structures have been proposed as vinyl benzyl ether resins improved in those characteristics, and an attempt to suppress a change in dielectric loss tangent of each of the resins when the resin is subjected to severe thermal history, and an attempt to improve the heat resistance thereof have been made. However, it cannot be said yet that the characteristic improvements are sufficient, and hence further characteristic improvements have been desired. Accordingly, the resins have not been sufficient as mounting materials in terms of reliability and processability (Patent Literature 3, Patent Literature 4, and Patent Literature 5).

In addition, there is a disclosure of a polyfunctional vinyl resin composition characterized by containing a polyfunctional vinyl resin obtained by subjecting a hydroxy group of at least one kind selected from the group consisting of: a phenol aralkyl resin; a naphthol aralkyl resin; a biphenyl-type phenol novolac resin; and a biphenyl-type naphthol novolac resin to vinyl benzyl etherification (Patent Literature 6). However, the vinyl benzyl etherified polyfunctional vinyl resin synthesized in accordance with the production method disclosed in the literature has a large total halogen content and a large residual vinyl aromatic halomethyl compound amount. Accordingly, the resin has not been satisfactory as an insulating material adapted to a high frequency in terms of dielectric loss tangent and heat resistance after the resin has been subjected to severe thermal history. In addition, the resin has not been desirable in terms of moldability because the resin is liable to cause a molding failure.

In addition, it has been known that a phenolic hydroxy group of a polyfunctional phenylene ether oligomer, which is obtained by causing a polyhydric phenol having 3 or more and less than 9 phenolic hydroxy groups in a molecule thereof, and having an alkyl group or an alkylene group at its 2- or 6-position with respect to at least one phenolic hydroxy group out of the groups, and a monohydric phenol compound to react with each other, is subjected to vinyl benzylation (Patent Literature 7). However, a vinyl benzyl ether resin obtained by the technology has involved the following drawbacks: the resin has a high molding processing temperature owing to the fact that its viscosity is high; and when the resin is exposed to high temperatures under an air atmosphere, its dielectric loss tangent largely deteriorates.

As described above, none of the related-art vinyl benzyl ether resins has provided a cured article having heat resistance satisfying a low dielectric loss tangent after severe thermal history enabling the cured article to resist lead-free solder processing, the heat resistance being required in an electrically insulating material application, in particular, the application of an electrically insulating material adapted to a high frequency. In addition, the resins have been insufficient in terms of reliability and processability.

CITATION LIST

Patent Literature

[PTL 1] JP 63-68537 A
[PTL 2] JP 64-65110 A
[PTL 3] JP 01-503238 A
[PTL 4] JP 09-31006 A
[PTL 5] JP 2004-323730 A
[PTL 6] JP 2003-306591 A
[PTL 7] JP 2007-308685 A

SUMMARY OF INVENTION

An object of the present invention is to provide a vinyl resin and a resin composition each providing a cured article, which shows a small change in dielectric characteristic after having been subjected to severe thermal history, shows a high thermal conductivity, and has a high glass transition temperature while having a low dielectric constant and a low dielectric loss tangent. Another object of the present invention is to provide a resin composition or a cured article, or a material including the resin composition or the cured article, the resin composition, the cured article, or the material being usable as a dielectric material, an insulating material, or a heat-resistant material in a field, such as an electrical and electronic industry, or a space and aircraft industry.

The inventors of the present invention have made extensive investigations while paying attention to a resin structure and a functional group, and as a result, have found that the above-mentioned problems can be solved by a polyfunctional vinyl resin obtained by the aromatic vinylation of a phenolic hydroxy group of a polyhydric hydroxy resin having, as a substituent, a dicyclopentenyl group obtained from a reaction between a 2,6-disubstituted phenol and dicyclopentadiene. Thus, the inventors have completed the present invention.

That is, according to one embodiment of the present invention, there is provided a polyfunctional vinyl resin, which is represented by the following general formula (1):

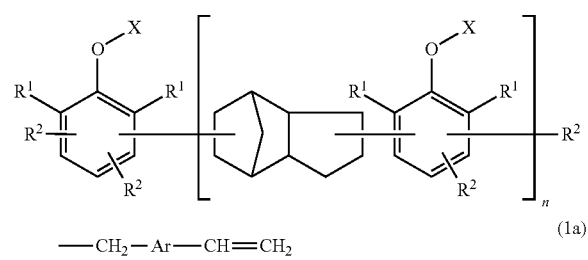

where
- $R^1$s each independently represent a hydrocarbon group having 1 to 8 carbon atoms,
- $R^2$s each independently represent a hydrogen atom or a dicyclopentenyl group, and at least one thereof represents a dicyclopentenyl group,
- Xs each independently represent a hydrogen atom or a vinyl group-containing aromatic group represented by the formula (1a), and at least one thereof represents a vinyl group-containing aromatic group, and
- "n" represents a number of repetitions, and an average thereof is a number of from 1 to 5.
- Ar in the formula (1a) represents an aromatic ring, and preferably represents an aromatic ring selected from the group consisting of: a benzene ring; a naphthalene ring; and a biphenyl ring. The aromatic ring Ar may be unsubstituted, or may have one or more substituents.

According to another embodiment of the present invention, there is provided a method of producing the polyfunctional vinyl resin, including: causing dicyclopentadiene to react at a ratio of from 0.28-fold mol to 2-fold mol with 1 mol of a 2,6-disubstituted phenol represented by the following general formula (2) to provide a polyhydric hydroxy resin represented by the following general formula (3); and then causing the resultant polyhydric hydroxy resin and an aromatic vinylating agent represented by the following general formula (4) to react with each other:

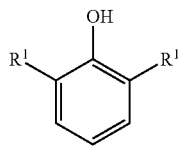

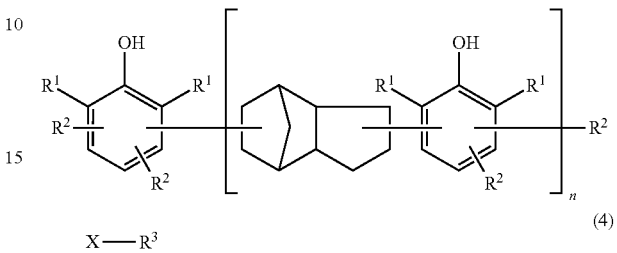

where
- $R^1$, $R^2$, X, and "n" are each identical in meaning to the definition in the general formula (1), and
- $R^3$ represents a halogen.

According to another embodiment of the present invention, there are provided a polyfunctional vinyl resin composition, including, as essential components: a polyfunctional vinyl resin; and a radical polymerization initiator, and a polyfunctional vinyl resin cured article, which is obtained by curing the composition.

According to another embodiment of the present invention, there are provided a prepreg, including: a semi-cured article of the polyfunctional vinyl resin composition; and a fibrous base material, a resin sheet, including: a resin layer containing the semi-cured article of the polyfunctional vinyl resin composition; and a supporting film, and a laminated plate, which is molded by laminating the prepreg and/or the resin sheet.

Each of the polyfunctional vinyl resin and composition of the present invention, and the cured article obtained by curing the composition is useful as a material reduced in signal loss because each of the resin, the composition, and the cured article has a high thermal conductivity while having a low dielectric constant and a low dielectric loss tangent, and hence facilitates the escape of heat generated from an electronic part or wiring when used as an electronic material for a high-speed communication device. In particular, each of the resin, the composition, and the cured article can maintain an excellent dielectric characteristic even when subjected to high-temperature thermal history under an air atmosphere, and hence has high reliability in terms of electrical characteristic even under severe use conditions.

DESCRIPTION OF EMBODIMENTS

Figure 1:
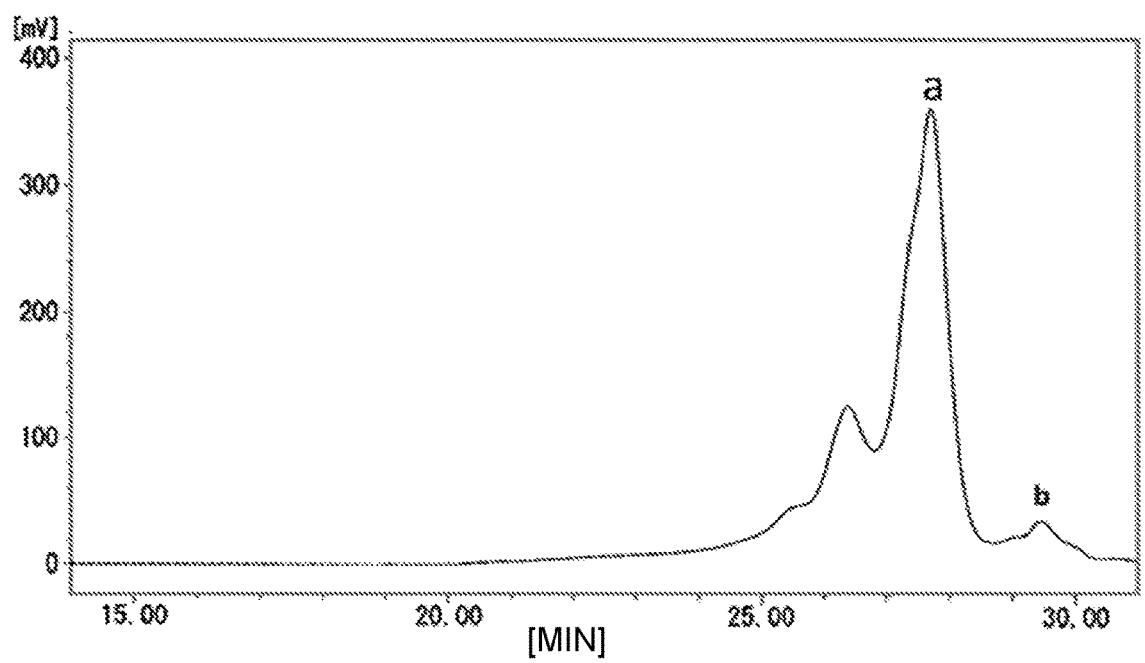
FIG. 1 is an illustration of a GPC chart of a polyhydric hydroxy resin obtained in Synthesis Example 1.

The present invention is described in detail below.

A polyfunctional vinyl resin of the present invention is represented by the general formula (1).

In the general formula (1), $R^1$ represents a hydrocarbon group having 1 to 8 carbon atoms, preferably an alkyl group having 1 to 8 carbon atoms, an aryl group having 6 to 8 carbon atoms, an aralkyl group having 7 or 8 carbon atoms, or an allyl group. The alkyl group having 1 to 8 carbon atoms may be any of linear, branched, and cyclic alkyl groups, and examples thereof include, but not limited to: hydrocarbon groups, such as a methyl group, an ethyl group, a n-propyl group, an isopropyl group, a n-butyl group, a sec-butyl group, an isobutyl group, a t-butyl group, a n-pentyl group, an isopentyl group, a neopentyl group, a t-pentyl group, a methylbutyl group, a n-hexyl group, a dimethylbutyl group, a n-heptyl group, a methylhexyl group, a trimethylbutyl group, a n-octyl group, a dimethylpentyl group, an ethylpentyl group, an isooctyl group, and an ethylhexyl group; and cycloalkyl groups each having 5 to 8 carbon atoms, such as a cyclohexyl group, a cycloheptyl group, a cyclooctyl group, a methylcyclohexyl group, a dimethylcyclohexyl group, an ethylcyclohexyl group, and a methylcycloheptyl group. Examples of the aryl group having 6 to 8 carbon atoms include, but not limited to, a phenyl group, a tolyl group, a xylyl group, and an ethylphenyl group. Examples of the aralkyl group having 7 or 8 carbon atoms include, but not limited to, a benzyl group and an α-methylbenzyl group. Of those substituents, a methyl group or a phenyl group is preferred from the viewpoints of ease of availability and reactivity at the time of the formation of a cured article from the resin, and a methyl group is particularly preferred.

$R^2$s described above each independently represent a hydrogen atom or a dicyclopentenyl group, and at least one thereof represents a dicyclopentenyl group. The dicyclopentenyl group is a group derived from dicyclopentadiene, and is represented by the following formula (1b) or formula (1c).

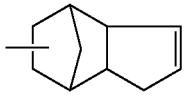

(1b)

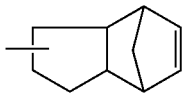

(1c)

Xs each independently represent a hydrogen atom or a vinyl group-containing aromatic group represented by the formula (1a), and at least one thereof represents a vinyl group-containing aromatic group, which is a group derived from an aromatic vinylating agent serving as a raw material for the polyfunctional vinyl resin. Ar in the formula (1a) represents an aromatic ring selected from the group consisting of: a benzene ring; a naphthalene ring; and a biphenyl ring.

The aromatic ring Ar may be unsubstituted, or may have one or more substituents. When the ring has a substituent, the number of the substituents is preferably from 1 to 4, and the substituent is preferably an alkyl group having 1 to 10 carbon atoms or an aryl group, more preferably an alkyl group having 1 to 3 carbon atoms or a phenyl group.

"n" represents a number of repetitions, and represents a number of 1 or more. The average thereof represents a number of from 1 to 5, preferably from 1.1 to 4.0, more preferably from 1.2 to 3.0, still more preferably from 1.3 to 2.0. The average is a number average.

Contents measured by GPC preferably fall within the following ranges: the content of an n=0 form is 10 area % or less; the content of an n=1 form is from 50 area % to 70 area %; and the content of n=2 or more forms is from 20 area % to 40 area %.

The number-average molecular weight (Mn) of the polyfunctional vinyl resin of the present invention is preferably from 400 to 3,000, more preferably from 500 to 1,500. The vinyl equivalent (g/eq.) thereof is preferably from 200 to 600, more preferably from 220 to 550, still more preferably from 300 to 550, particularly preferably from 400 to 500. The total chlorine amount thereof is preferably 1,500 ppm or less, more preferably 1,300 ppm or less.

The polyfunctional vinyl resin of the present invention may be suitably obtained by causing a polyhydric hydroxy resin represented by the general formula (3) and an aromatic vinylating agent represented by the general formula (4) to react with each other.

The polyhydric hydroxy resin represented by the general formula (3) is obtained by, for example, a method including causing dicyclopentadiene to react at a predetermined ratio with a 2,6-disubstituted phenol represented by the general formula (2), and dicyclopentadiene may be continuously added, or may be added in several stages (divided sequential addition in which dicyclopentadiene is added twice or more) and intermittently caused to react therewith. The ratio of dicyclopentadiene is from 0.28-fold mol to 2-fold mol with respect to 1 mol of the 2,6-disubstituted phenol. When dicyclopentadiene is continuously added and caused to react with the 2,6-disubstituted phenol, the ratio of dicyclopentadiene is from 0.25-fold mol to 1-fold mol, preferably from 0.28-fold mol to 1-fold mol, more preferably from 0.3-fold mol to 0.5-fold mol with respect to 1 mol of the 2,6-disubstituted phenol. When dicyclopentadiene is added in a divided sequential manner and caused to react with the 2,6-disubstituted phenol, the ratio of dicyclopentadiene as a whole is preferably from 0.8-fold mol to 2-fold mol, more preferably from 0.9-fold mol to 1.7-fold mol. The usage ratio of dicyclopentadiene at each stage is preferably from 0.28-fold mol to 1-fold mol.

Examples of the 2,6-disubstituted phenol include 2,6-dimethylphenol, 2,6-diethylphenol, 2,6-dipropylphenol, 2,6-diisopropylphenol, 2,6-di(n-butyl) phenol, 2,6-di(t-butyl) phenol, 2,6-dihexylphenol, 2,6-dicyclohexylphenol, and 2,6-diphenylphenol. Of those, 2,6-diphenylphenol and 2,6-dimethylphenol are preferred from the viewpoints of ease of availability and reactivity at the time of the formation of a cured article from the resin, and 2,6-dimethylphenol is particularly preferred.

A catalyst to be used for a reaction between the phenol and dicyclopentadiene is a Lewis acid, and is specifically, for example, a boron trifluoride compound, such as boron trifluoride, a boron trifluoride-phenol complex, or a boron trifluoride-ether complex, a metal chloride, such as aluminum chloride, tin chloride, zinc chloride, titanium tetrachloride, or iron chloride, or an organic sulfonic acid, such as methanesulfonic acid, ethanesulfonic acid, or propanesulfonic acid. Of those, a boron trifluoride-ether complex is preferred from the viewpoint of ease of handleability. When the catalyst is the boron trifluoride-ether complex, its usage amount is from 0.001 part by mass to 20 parts by mass, preferably from 0.5 part by mass to 10 parts by mass with respect to 100 parts by mass of dicyclopentadiene.

A method for the reaction is desirably a system including: loading the 2,6-disubstituted phenol and the catalyst into a reactor; and dropping dicyclopentadiene thereinto over from 1 hr to 10 hr.

A reaction temperature is preferably from 50° C. to 200° C., more preferably from 100° C. to 180° C., still more preferably from 120° C. to 160° C. A reaction time is preferably from 1 hr to 10 hr, more preferably from 3 hr to 10 hr, still more preferably from 4 hr to 8 hr.

After the completion of the reaction, an alkali, such as sodium hydroxide, potassium hydroxide, or calcium hydroxide, is added to deactivate the catalyst. After that, a solvent, such as an aromatic hydrocarbon, such as toluene or xylene, or a ketone, such as methyl ethyl ketone or methyl isobutyl ketone, is added to dissolve the resultant, and the solution is washed with water, followed by the recovery of the solvent under reduced pressure. Thus, the target polyhydric hydroxy resin can be obtained. The following is preferably performed: the total amount of dicyclopentadiene is caused to react with the 2,6-disubstituted phenol as soon as possible; and part, preferably 10% or less of the 2,6-disubstituted phenol is left unreacted, and is recovered under reduced pressure.

Also for the reaction, a solvent, such as an aromatic hydrocarbon, such as benzene, toluene, or xylene, a halogenated hydrocarbon, such as chlorobenzene or dichlorobenzene, an ether, such as ethylene glycol dimethyl ether or diethylene glycol dimethyl ether, or a ketone, such as methyl isobutyl ketone, cyclopentanone, or cyclohexanone, may be used as required for viscosity adjustment or the like.

Mass spectrometry (MS) and a Fourier transform infrared spectrophotometer (FT-IR) measurement method may each be used as a method of recognizing that the above-mentioned dicyclopentenyl group has been introduced into the above-mentioned polyhydric hydroxy resin.

When the mass spectrometry is used, electrospray ionization mass spectrometry (ESI-MS), field desorption mass spectrometry (FD-MS), or the like may be used. The fact that the dicyclopentenyl group has been introduced can be recognized by subjecting a sample from which a component having a different number of nuclides has been separated by GPC or the like to the mass spectrometry.

In the case where the FT-IR measurement method is used, when a cell with a sample thin film obtained by applying the sample dissolved in an organic solvent such as THF onto a KRS-5 cell and drying the organic solvent is subjected to measurement with an FT-IR, a peak derived from C—O stretching vibration in a phenol nucleus appears near 1,210 cm-1, and only when a dicyclopentenyl group is introduced into the sample, a peak derived from the C—H stretching vibration of an olefin moiety in a dicyclopentadiene skeleton appears near 3,040 cm 1. When a line obtained by linearly connecting the start and end of a target peak is defined as a baseline, and a length from the top of the peak to the baseline is defined as a peak height, the introduction amount of the dicyclopentenyl group may be determined by the ratio $(A_{3040}/A_{1210})$ of the peak height of the peak near 3,040 cm$^{-1}$ $(A_{3040})$ to the peak height of the peak near 1,210 cm$^{-1}$ $(A_{1210})$. It has been able to be recognized that as the ratio becomes larger, a physical property value becomes more satisfactory. The ratio $(A_{3040}/A_{1210})$ for satisfying a target physical property is preferably 0.05 or more, more preferably 0.10 or more, particularly preferably from 0.10 to 0.30.

The hydroxy group equivalent of the polyfunctional hydroxy resin is preferably from 150 to 500, more preferably from 200 to 350. The average molecular weights thereof are as follows: the weight-average molecular weight (Mw) thereof is preferably from 500 to 2,000, more preferably from 600 to 900; and the number-average molecular weight (Mn) thereof is preferably from 350 to 1,200, more preferably from 400 to 600. The softening point thereof is preferably from 70° C. to 120° C., more preferably from 70° C. to 110° C.

The polyfunctional vinyl resin of the present invention may be suitably obtained by causing the polyhydric hydroxy resin represented by the general formula (3) thus obtained to react with the aromatic vinylating agent represented by the general formula (4).

A halomethylstyrene is preferred as the aromatic vinylating agent represented by the general formula (4). Specific examples of the halomethylstyrene include: chloromethylstyrene and bromomethylstyrene, and isomers thereof; and products obtained by substituting chloromethylstyrene and bromomethylstyrene with substituents. With regard to the substitution position of a halomethyl form, in the case of, for example, the halomethylstyrene, the substitution position is preferably a 4-position, and a 4-position form preferably accounts for 60 mass % or more of the entirety thereof.

The reaction between the polyhydric hydroxy resin and the halomethylstyrene serving as the aromatic vinylating agent may be performed in the absence of any solvent or in the presence of a solvent. The polyfunctional vinyl resin may be obtained by: adding the halomethylstyrene to the polyhydric hydroxy resin; adding a metal hydroxide to the mixture to perform the reaction; and removing the produced metal salt by a method, such as filtration or water washing.

The polyhydric hydroxy resin and the aromatic vinylating agent are desirably caused to react with each other at such a usage ratio that the vinyl equivalent of the aromatic vinylating agent is preferably from 0.5 equivalent to 1.5 equivalents, more preferably from 0.8 equivalent to 1.2 equivalents with respect to 1 equivalent of the hydroxy group equivalent of the polyhydric hydroxy resin.

Examples of the solvent include, but not limited to, benzene, toluene, xylene, methyl isobutyl ketone, diethylene glycol dimethyl ether, cyclopentanone, and cyclohexanone. Specific examples of the metal hydroxide include, but not limited to, sodium hydroxide and potassium hydroxide.

The reaction is performed at a temperature of 100° C. or less, preferably 80° C. or less, and when concern is raised about the self-polymerization of the halomethylstyrene serving as the aromatic vinylating agent, polymerization inhibitors, such as quinones, a nitro compound, nitrophenols, a nitroso compound, a nitrone compound, and oxygen, may each be used.

A reaction endpoint may be determined by tracking the remaining amount of the halomethylstyrene serving as the aromatic vinylating agent with any one of various chromatograms, and a reaction rate may be adjusted by an adjustment method, such as the adjustment of the kind or amount of the metal hydroxide, the adjustment of the addition rate thereof, or the utilization of an appropriate catalyst.

Although the polyfunctional vinyl resin of the present invention may be cured alone, it is suitable that the resin be used as a polyfunctional resin composition blended with any one of various additives. For example, the resin may be cured after having been blended with a radical polymerization initiator for accelerating its curing.

With regard to the radical polymerization initiator (also referred to as "radical polymerization catalyst"), for example, the resin composition of the present invention, which causes a crosslinking reaction through a method such as heating to cure as described later, may be used after the radical polymerization initiator has been incorporated thereinto for the purpose of reducing a reaction temperature at the time or accelerating the crosslinking reaction of an unsaturated group thereof. The amount of the radical polymerization initiator to be used for the purpose is preferably from 0.01 part by mass to 12 parts by mass, more preferably from 0.1 part by mass to 8 parts by mass with respect to 100 parts by mass of the polyfunctional vinyl resin.

Typical examples of the radical polymerization initiator include, but not limited to, peroxides, such as benzoyl peroxide, cumene hydroperoxide, 2,5-dimethylhexane-2,5-dihydroperoxide, 2,5-dimethyl-2,5-di(t-butylperoxy) hexyne-3, di-t-butyl peroxide, t-butylcumyl peroxide, α,α'-bis(t-butylperoxy-m-isopropyl)benzene, 2,5-dimethyl-2,5-di(t-butylperoxy) hexane, dicumyl peroxide, di-t-butyl peroxyisophthalate, t-butyl peroxybenzoate, 2,2-bis(t-butylperoxy) butane, 2,2-bis(t-butylperoxy) octane, 2,5-dimethyl-2,5-di(benzoylperoxy) hexane, di(trimethylsilyl) peroxide, and trimethylsilyl triphenylsilyl peroxide. In addition, 2,3-dimethyl-2,3-diphenylbutane may be used as the radical polymerization initiator (or polymerization catalyst), though 2,3-dimethyl-2,3-diphenylbutane is not a peroxide. However, the catalyst or the radical polymerization initiator to be used in the curing of the resin composition is not limited to those examples.

The polyfunctional vinyl resin composition of the present invention may be blended with a vinyl resin except the polyfunctional vinyl resin of the present invention or any other thermal polyfunctional vinyl resin. Examples thereof include a vinyl ester resin, a polyvinylbenzyl resin, an epoxy resin, an oxetane resin, a maleimide resin, an acrylate resin, a polyester resin, a polyurethane resin, a polycyanate resin, a phenol resin, and a benzoxazine resin.

In addition, for example, thermoplastic resins, such as a polystyrene resin, a polyphenylene ether resin, a polyetherimide resin, a polyethersulfone resin, a PPS resin, a polycyclopentadiene resin, and a polycycloolefin resin, thermoplastic elastomers, such as a styrene-ethylene-propylene copolymer, a styrene-ethylene-butylene copolymer, a styrene-butadiene copolymer, a styrene-isoprene copolymer, a hydrogenated styrene-butadiene copolymer, and a hydrogenated styrene-isoprene copolymer, and rubbers, such as polybutadiene and polyisoprene, may each be blended.

Various known flame retardants may each be used in the polyfunctional vinyl resin composition of the present invention for the purpose of improving the flame retardancy of a cured article to be obtained to the extent that its reliability is not reduced. Examples of the usable flame retardants include a halogen-based flame retardant, a phosphorus-based flame retardant, a nitrogen-based flame retardant, a silicone-based flame retardant, an inorganic flame retardant, and an organometallic salt-based flame retardant. From an environmental viewpoint, a halogen-free flame retardant is preferred, and a phosphorus-based flame retardant is particularly preferred. Those flame retardants may be used alone, two or more kinds of the flame retardants of the same system may be used in combination, or the flame retardants of different systems may be used in combination.

The polyfunctional vinyl resin composition of the present invention may include a component except those listed above for the purpose of further improving its functionality. Examples of such other component include a filler, a UV inhibitor, an antioxidant, a coupling agent, a plasticizer, flux, a thixotropy-imparting agent, a smoothing agent, a colorant, a pigment, a dispersant, an emulsifying agent, an elasticity-reducing agent, a release agent, an antifoaming agent, and an ion-trapping agent.

Examples of the filler include: inorganic fillers, such as molten silica, crystalline silica, alumina, silicon nitride, boron nitride, aluminum nitride, aluminum hydroxide, calcium hydroxide, magnesium hydroxide, boehmite, talc, mica, clay, calcium carbonate, magnesium carbonate, barium carbonate, zinc oxide, titanium oxide, magnesium oxide, magnesium silicate, calcium silicate, zirconium silicate, barium sulfate, and carbon; fibrous fillers, such as a carbon fiber, a glass fiber, an alumina fiber, a silica alumina fiber, a silicon carbide fiber, a polyester fiber, a polyamide fiber, a cellulose fiber, an aramid fiber, and a ceramic fiber; and a fine particle rubber.

Examples of the other components include additives, such as: organic pigments, such as quinacridone-based, azo-based, and phthalocyanine-based pigments; inorganic pigments, such as titanium oxide, a metal foil-like pigment, and an anti-rust pigment; UV absorbers, such as hindered amine-based, benzotriazole-based, and benzophenone-based UV absorbers; antioxidants, such as hindered phenol-based, phosphorus-based, sulfur-based, and hydrazide-based antioxidants; release agents, such as stearic acid, palmitic acid, zinc stearate, and calcium stearate; a leveling agent; a rheology control agent; a pigment dispersant; a cissing inhibitor; and a defoaming agent. The blending amount of each of those other components preferably falls within the range of from 0.01 mass % to 20 mass % with respect to the total solid content in the resin composition.

The polyfunctional vinyl resin composition of the present invention may be turned into a resin varnish by being dissolved in a solvent. Examples of the solvent include methyl ethyl ketone, acetone, toluene, xylene, tetrahydrofuran, dioxolane, dimethylformamide, methyl isobutyl ketone, methoxypropanol, cyclohexanone, methylcellosolve, ethyl diglycol acetate, propylene glycol monomethyl ether acetate, and γ-butyrolactone. The solvent or its proper usage amount may be appropriately selected in accordance with applications. For example, in a printed wiring board application, a solvent having a boiling point of 160° C. or less, such as methyl ethyl ketone, acetone, toluene, xylene, or 1-methoxy-2-propanol, is preferred, and the solvent is preferably used at such a ratio that a non-volatile content of from 20 mass % to 80 mass % is achieved. Meanwhile, for example, the following solvent is preferably used in a build-up adhesive film application: a ketone, such as acetone, methyl ethyl ketone, or cyclohexanone; an ester compound, such as ethyl acetate, butyl acetate, cellosolve acetate, propylene glycol monomethyl ether acetate, carbitol acetate, or γ-butyrolactone; cellosolve; a carbitol such as butylcarbitol; an aromatic hydrocarbon, such as toluene or xylene; dimethylformamide; dimethylacetamide; or N-methylpyrrolidone. In addition, the solvent is preferably used at such a ratio that a non-volatile content of from 20 mass % to 80 mass % is achieved. A laminated plate of the present invention is obtained by curing the resin varnish. Specific examples thereof include a printed wiring board, a printed circuit board, a flexible printed wiring board, and a build-up wiring board.

A cured article obtained by curing the polyfunctional vinyl resin composition of the present invention may be used as a molded article, a laminated article, a cast article, an adhesive, a coating, or a film. For example, a cured article of a semiconductor sealing material is a cast article or a molded article, and the cured article for this application may be obtained by a method including: casting the compound, or molding the compound with a transfer molding machine, an injection molding machine, or the like; and heating the resultant at from 80° C. to 230° C. for from 0.5 hr to 10 hr. In addition, a cured article of a resin varnish is a laminated article, and the cured article may be obtained by a method including: impregnating a base material, such as the above-mentioned fibrous filler or paper, with the resin varnish;

drying the resultant by heating to provide a prepreg; and laminating the prepregs alone, or laminating the prepreg and a metal foil such as a copper foil, followed by heat press molding.

In addition, the polyfunctional vinyl resin composition of the present invention is useful as a material for an electronic part, in particular, a high frequency electronic part material by blending therein inorganic high-dielectric powder such as barium titanate, or an inorganic magnetic material such as a ferrite.

Next, the prepreg of the present invention and the cured article thereof are described. In the prepreg of the present invention, a base material is added in order to enhance mechanical strength and improve dimensional stability.

Examples of such base material include fabrics or papers including: various glass fabrics, such as a roving cloth, a cloth, a chopped mat, and a surfacing mat; asbestos fabrics; metal fiber fabrics and other synthetic or natural inorganic fiber fabrics; woven fabrics or non-woven fabrics each obtained from a liquid crystal fiber, such as a wholly aromatic polyamide fiber, a wholly aromatic polyester fiber, or a polybenzazole fiber; woven fabrics or non-woven fabrics each obtained from a synthetic fiber, such as a polyvinyl alcohol fiber, a polyester fiber, or an acrylic fiber; natural fiber fabrics, such as a cotton fabric, a hemp fabric, or a felt; and natural cellulose-based fabrics, such as a carbon fiber fabric, kraft paper, cotton paper, or paper-glass-mixed fiber paper. Those base materials may be used alone or in combination thereof.

It is desired that the ratio of the base material be from 5 mass % to 90 mass %, preferably from 10 mass % to 80 mass %, more preferably from 20 mass % to 70 mass % in the prepreg. When the ratio of the base material is less than 5 mass %, the dimensional stability and strength of the cured article tend to decrease. In addition, when the ratio of the base material is more than 90 mass %, the dielectric characteristics of the cured article tend to lower.

In the prepreg of the present invention, as required, a coupling agent may be used for the purpose of improving an adhesive property at an interface between the resin and the base material. A general coupling agent, such as a silane coupling agent, a titanate coupling agent, an aluminum-based coupling agent, or a zircoaluminate coupling agent, may be used as the coupling agent.

As a method of producing the prepreg of the present invention, for example, there is given a method involving homogeneously dissolving or dispersing the polyfunctional vinyl resin composition of the present invention and as required any other component in the above-mentioned aromatic or ketone-based solvent or a mixed solvent thereof, and impregnating the base material with the resultant, followed by drying. The impregnation is performed by dipping, application, or the like. The impregnation may be repeated a plurality of times as required, and in this case, the impregnation may be repeated using a plurality of solutions different from each other in composition or concentration to finally adjust the resin composition and the resin amount to desired ones.

The cured article is obtained through the curing of the prepreg of the present invention by a method such as heating. A production method therefor is not particularly limited, and a cured article (laminated plate) having a desired thickness may be obtained by, for example, laminating the plurality of prepregs, and bonding the respective layers under heating and pressurization, and at the same time, performing thermal curing. In addition, a multilayer laminated body having a new layer configuration may be obtained by combining the cured article in which the plurality of prepregs have been bonded and cured once, and another prepreg. Although the lamination molding and the curing are typically performed with, for example, a heat press at the same time, both the operations may each be performed separately. That is, an uncured or semi-cured prepreg obtained in advance by the lamination molding may be cured through heat treatment or treatment by another method.

The molding and the curing may be performed, for example, in the ranges of a temperature of from 80° C. to 300° C., a pressure of from 0.1 kgf/cm$^2$ to 1,000 kgf/cm$^2$, and a period of time of from 1 min to 10 hr, more preferably the ranges of a temperature of from 150° C. to 250° C., a pressure of from 1 kgf/cm$^2$ to 500 kgf/cm$^2$, and a period of time of from 1 min to 5 hr.

A laminated body of the present invention includes a layer of the prepreg of the present invention and a layer of a metal foil. Examples of the metal foil to be used in this case include a copper foil and an aluminum foil. The thickness thereof is not particularly limited, but falls within the range of from 3 μm to 200 μm, more preferably from 5 μm to 105 μm.

A method of producing the laminated body of the present invention may be, for example, a method including: laminating the above-mentioned prepreg obtained from the polyfunctional vinyl resin composition of the present invention and the base material, and the metal foil in a layer configuration in accordance with purposes; and bonding the respective layers under heating and pressurization, and at the same time, performing thermal curing. In the laminated body of the polyfunctional vinyl resin composition of the present invention, the cured article and the metal foil are laminated in any layer configuration. The metal foil may be used as a surface layer or as an intermediate layer. In addition to the foregoing, the lamination and the curing may each be repeated a plurality of times to form a multilayer structure.

An adhesive may be used for the bonding to the metal foil. Examples of the adhesive include, but not particularly limited to, an epoxy-based adhesive, an acrylic adhesive, a phenol-based adhesive, and a cyanoacrylate-based adhesive. The lamination molding and the curing may be performed under similar conditions to those in the production of the cured article of the prepreg of the present invention.

In addition, the polyfunctional vinyl resin composition of the present invention may be molded into a film shape. The thickness thereof is not particularly limited, but falls within the range of from 3 μm to 200 μm, more preferably from 5 μm to 105 μm.

A method of producing the film of the present invention is not particularly limited, and an example thereof is a method involving homogeneously dissolving or dispersing the polyfunctional vinyl resin composition, and as required, any other component in, for example, an aromatic or ketone-based solvent or a mixed solvent thereof, and applying the resultant to a resin film such as a PET film, followed by drying. The application may be repeated a plurality of times as required, and in this case, the application may be repeated using a plurality of solutions different from each other in composition or concentration to finally adjust the resin composition and the resin amount to desired ones.

In addition, a metal foil with a resin may be obtained from the polyfunctional vinyl resin composition of the present invention and a metal foil. Examples of the metal foil to be used in this case include a copper foil and an aluminum foil.

The thickness thereof is not particularly limited, but falls within the range of from 3 μm to 200 μm, more preferably from 5 μm to 105 μm.

A method of producing the metal foil with a resin is not particularly limited, and an example thereof is a method involving homogeneously dissolving or dispersing the polyfunctional vinyl resin composition, and as required, any other component in, for example, an aromatic or ketone-based solvent or a mixed solvent thereof, and applying the resultant to a metal foil, followed by drying. The application may be repeated a plurality of times as required, and in this case, the application may be repeated using a plurality of solutions different from each other in composition or concentration to finally adjust the resin composition and the resin amount to desired ones.

A substrate for an electronic material is obtained by using the laminated body of the present invention. The substrate for an electronic material may be suitably used as a part for any of various electrical and electronic devices required to have reliability under an environment where heat resistance and water resistance are required and to have transmission reliability of a high frequency signal, such as a cellular phone, a PHS, a notebook computer, a personal digital assistant (PDA), a portable video phone, a personal computer, a supercomputer, a server, a router, a liquid crystal projector, an engineering workstation (EWS), a pager, a word processor, a television, a viewfinder-type or monitor direct-view-type video tape recorder, an electronic organizer, an electronic desk calculator, a car navigation system, a POS terminal, and a device having a touch panel. In particular, the electrical and electronic part may be suitably used as a circuit board for the electrical and electronic devices by virtue of the thermal stability of the excellent dielectric characteristics of the cured article of the present invention, and its dimensional stability and moldability compatible with fine-pattern circuit formation. Specific examples of the circuit board include a single-sided, double-sided, or multilayer printed board, a flexible substrate, and a build-up substrate. The multilayer circuit board using the metal plating as the conductor layer is also included as a preferred example.

EXAMPLES

The present invention is described more specifically by way of Examples and Comparative Examples. The term "part(s)" means "part(s) by mass," and the term "%" means "mass %" unless otherwise stated. All equivalents are represented in a g/eq. unit.

Test conditions for a polyhydric hydroxy resin, a vinyl resin, and a cured article are described.
(1) Hydroxy Group Equivalent:
Measurement was performed in conformity with the JIS K 0070 standard.
Specifically, a potentiometric titration apparatus was used, 1,4-dioxane was used as a solvent, acetylation was performed with 1.5 mol/L acetyl chloride, and excess acetyl chloride was decomposed with water, followed by titration with 0.5 mol/L potassium hydroxide. Unless otherwise stated, the hydroxy group equivalent of the polyhydric hydroxy resin means a phenolic hydroxy group equivalent.
(2) Vinyl Equivalent:
Measurement was performed in conformity with the JIS K 0070 standard. Specifically, Wijs solution (solution of iodine monochloride) was caused to react with a sample, and the resultant was left to stand in a dark place. After that, excess iodine chloride was reduced to iodine, and the iodine content of the sample was titrated with sodium thiosulfate, followed by the calculation of the iodine value thereof. The iodine value was converted into a vinyl equivalent.
(3) Total Chlorine Amount:
1.0 g of a sample was dissolved in 25 mL of butyl carbitol. After that, 25 mL of a 1 N solution of KOH in propylene glycol was added to the solution, and the mixture was heated to reflux for 10 min, and was then cooled to room temperature. 100 mL of 80% acetone water was further added to the cooled product, and the total chlorine amount of the sample was measured by subjecting the mixture to potentiometric titration with a 0.002 N aqueous solution of $AgNO_3$.
(4) Molecular Weight Distribution (Mw, Mn):
Measurement was performed as follows: a GPC measuring apparatus (manufactured by Tosoh Corporation, HLC-8220GPC) was used; the apparatus to be used was mounted with columns (manufactured by Tosoh Corporation, TSK Guard column, TSKgel G2000HXL, TSKgel G3000HXL, and TSKgel G4000HXL) in series; a refractive index detector (RI) was used as a detector; tetrahydrofuran (THF) was used as a solvent; and the measurement was performed at a flow rate of 1.0 mL/min and a column temperature of 40° C. 50 μL of a product obtained by dissolving 0.1 g of a sample in 10 mL of THF and filtering the solution with a microfilter was used as a measurement sample. A GPC-8020 model II version 6.00 manufactured by Tosoh Corporation was used in data processing.
(5) Thermal Conductivity:
Measurement was performed in conformity with the JIS R 1611 standard.
(6) Dielectric Constant and Dielectric Loss Tangent:
Measurement was performed in conformity with the JIS C 2565 standard. Specifically, a sample was dried in an oven set to 105° C. for 2 hr, and was allowed to cool in a desiccator, followed by the measurement of the values of its dielectric constant and dielectric loss tangent with a cavity resonator method dielectric constant-measuring apparatus manufactured by AET, Inc. at a measurement frequency of 1 GHz.
(7) Glass Transition Temperature (Tg):
Measurement was performed in conformity with the JIS C 6481 standard.
Specifically, the glass transition temperature of a sample was represented by the peak top of the tan δ thereof at the time of measurement with a dynamic viscoelasticity-measuring apparatus (manufactured by Hitachi High-Tech Science Corporation, EXSTAR DMS6100) under a temperature increase condition of 5° C./min.

Abbreviations to be used in Examples and Comparative Examples are as described below.
[Polyhydric Hydroxy Resin]
  P1: polyhydric hydroxy resin obtained in Synthesis Example 1
  P2: polyhydric hydroxy resin obtained in Synthesis Example 2
  P3: polyhydric hydroxy resin obtained in Synthesis Example 3
  P4: biphenyl aralkyl-type polyhydric hydroxy resin (manufactured by Meiwa Plastic Industries, Ltd., MEH-7851, phenol hydroxy group equivalent: 223)
  P5: phenol novolac resin (manufactured by Aica Kogyo Co., Ltd., BRG-555, phenol hydroxy group equivalent: 105)
[Vinyl Compound]
  HV3: vinyl compound (manufactured by Mitsubishi Gas Chemical Company, Inc., OPE-2ST,
  Mn: 1,187, vinyl group equivalent: 590)

PO: organic peroxide (manufactured by NOF Corporation, Perbutyl P)
AO: antioxidant (manufactured by Adeka Corporation, ADK STAB AO-60)

Synthesis Example 1

Figure 2:
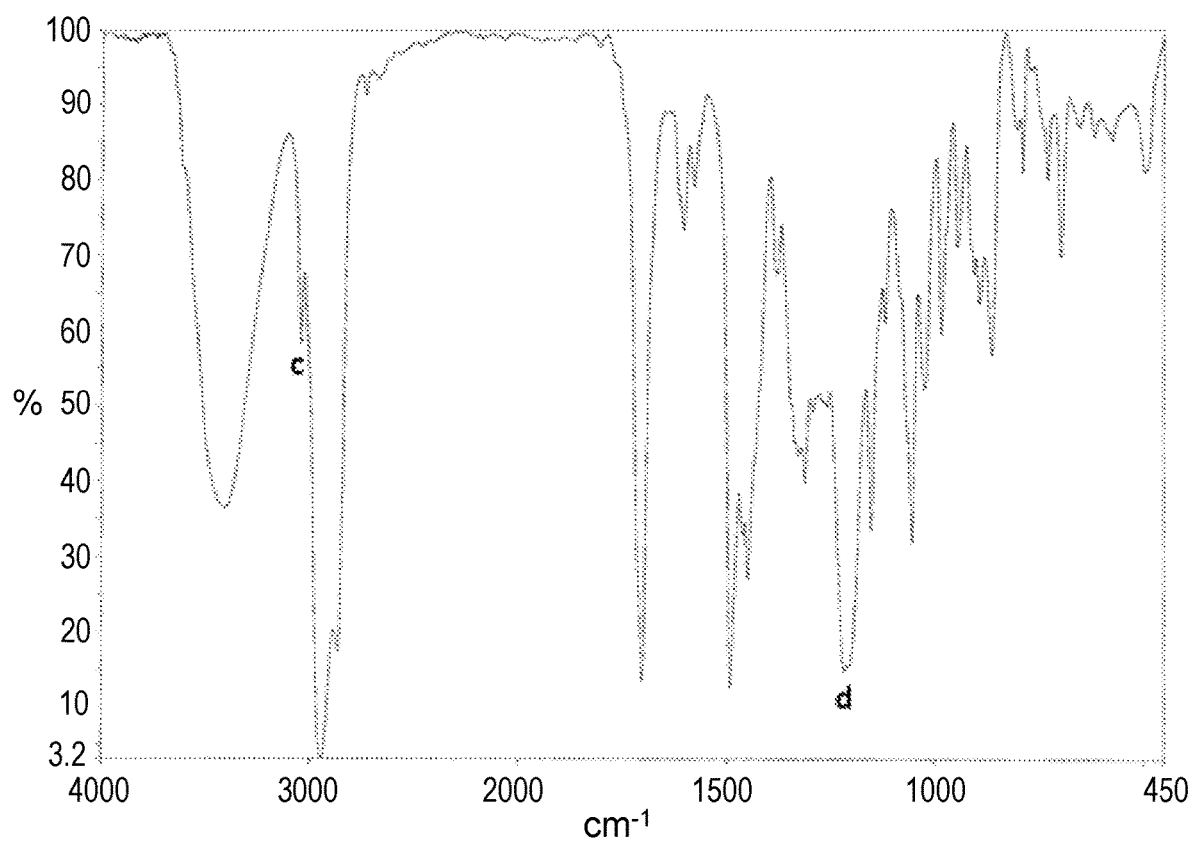
FIG. 2 is an illustration of an IR chart of the polyhydric hydroxy resin obtained in Synthesis Example 1.

140 parts of 2,6-xylenol and 9.3 parts (0.1-fold mol with respect to dicyclopentadiene to be added first) of a 47% $BF_3$-ether complex were loaded into a reaction apparatus formed of a glass-made separable flask including a stirring machine, a temperature gauge, a nitrogen-blowing tube, a dropping funnel, and a cooling tube, and the mixture was warmed to 110° C. while being stirred. While the mixture was held at the temperature, 86.6 parts (0.57-fold mol with respect to 2,6-xylenol) of dicyclopentadiene was dropped thereinto over 1 hr. Further, the mixture was subjected to a reaction at a temperature of 110° C. for 3 hr. After that, while the resultant was held at the temperature, 68 parts (0.44-fold mol with respect to 2,6-xylenol) of dicyclopentadiene was dropped thereinto over 1 hr. Further, the mixture was subjected to a reaction at 120° C. for 2 hr. 14.6 parts of calcium hydroxide was added to the resultant. Further, 45 parts of a 10% aqueous solution of oxalic acid was added thereto. After that, the mixture was warmed to 160° C. to be dehydrated, and was then warmed to 200° C. under a reduced pressure of 5 mmHg so that an unreacted raw material was removed by evaporation. 700 parts of MIBK was added to dissolve the product, and 200 parts of warm water at 80° C. was added to wash the solution, followed by the separation and removal of a water layer serving as a lower layer. After that, the residue was warmed to 160° C. under a reduced pressure of 5 mmHg so that MIBK was removed by evaporation. Thus, 274 parts of a reddish brown polyhydric hydroxy resin (P1) was obtained. The resin had a hydroxy group equivalent of 299, a softening point of 97° C., and an absorption ratio ($A_{3040}/A_{1210}$) of 0.17. As a result of the measurement of the mass spectrum of the resin by ESI-MS (negative), a peak was observed at an M– of each of 253, 375, 507, and 629. The GPC chart of the resultant polyhydric hydroxy resin (P1) is shown in FIG. 1, and the FT-IR chart thereof is shown in FIG. 2. The Mw and Mn of the resin measured by GPC were 690 and 510, respectively. In FIG. 1, "a" represents a mixed form of such a form that "n" in the formula (3) represents 1 and such a form that "n" in the formula (3) represents 1, the form being free of any $R^2$ adduct, and "b" represents such a form that "n" in the formula (3) represents 0. In FIG. 2, "c" represents a peak derived from the C—H stretching vibration of an olefin moiety in a dicyclopentadiene skeleton, and "d" represents absorption by C—O stretching vibration in a phenol nucleus.

Synthesis Example 2

140 parts of 2,6-xylenol and 9.3 parts (0.1-fold mol with respect to dicyclopentadiene to be added first) of a 47% $BF_3$-ether complex were loaded into the same reaction apparatus as that of Synthesis Example 1, and the mixture was warmed to 110° C. while being stirred. While the mixture was held at the temperature, 86.6 parts (0.57-fold mol with respect to 2,6-xylenol) of dicyclopentadiene was dropped thereinto over 1 hr. Further, the mixture was subjected to a reaction at a temperature of 110° C. for 3 hr. After that, while the resultant was held at the temperature, 90.6 parts (0.60-fold mol with respect to 2,6-xylenol) of dicyclopentadiene was dropped thereinto over 1 hr. Further, the mixture was subjected to a reaction at 120° C. for 2 hr. 14.6 parts of calcium hydroxide was added to the resultant. Further, 45 parts of a 10% aqueous solution of oxalic acid was added thereto. After that, the mixture was warmed to 160° C. to be dehydrated, and was then warmed to 200° C. under a reduced pressure of 5 mmHg so that an unreacted raw material was removed by evaporation. 740 parts of MIBK was added to dissolve the product, and 200 parts of warm water at 80° C. was added to wash the solution, followed by the separation and removal of a water layer serving as a lower layer. After that, the residue was warmed to 160° C. under a reduced pressure of 5 mmHg so that MIBK was removed by evaporation. Thus, 310 parts of a reddish brown polyhydric hydroxy resin (P2) was obtained. The resin had a hydroxy group equivalent of 341, a softening point of 104° C., and an absorption ratio ($A_{3040}/A_{1210}$) of 0.27. As a result of the measurement of the mass spectrum of the resin by ESI-MS (negative), a peak was observed at an M– of each of 253, 375, 507, and 629. The Mw and Mn of the resin measured by GPC were 830 and 530, respectively.

Synthesis Example 3

970 parts of 2,6-xylenol and 14.5 parts of a 47% $BF_3$-ether complex were loaded into the same reaction apparatus as that of Synthesis Example 1, and the mixture was warmed to 70° C. while being stirred. While the mixture was held at the temperature, 300 parts (0.29-fold mol with respect to 2,6-xylenol) of dicyclopentadiene was dropped thereinto over 2 hr. Further, the mixture was subjected to a reaction at a temperature of from 125° C. to 135° C. for 6 hr, and 2.3 parts of calcium hydroxide was added to the resultant. Further, 4.6 parts of a 10% aqueous solution of oxalic acid was added thereto. After that, the mixture was warmed to 160° C. to be dehydrated, and was then warmed to 200° C. under a reduced pressure of 5 mmHg so that an unreacted raw material was removed by evaporation. 1,000 parts of MIBK was added to dissolve the product, and 400 parts of warm water at 80° C. was added to wash the solution, followed by the separation and removal of a water layer serving as a lower layer. After that, the residue was warmed to 160° C. under a reduced pressure of 5 mmHg so that MIBK was removed by evaporation. Thus, 540 parts of a reddish brown polyhydric hydroxy resin (P3) was obtained. The resin had a hydroxy group equivalent of 213, a softening point of 71° C., and an absorption ratio ($A_{3040}/A_{1210}$) of 0.11. As a result of the measurement of the mass spectrum of the resin by ESI-MS (negative), a peak was observed at an M– of each of 253, 375, 507, and 629. The Mw and Mn of the resin measured by GPC were 670 and 520, respectively.

Example 1

Figure 3:
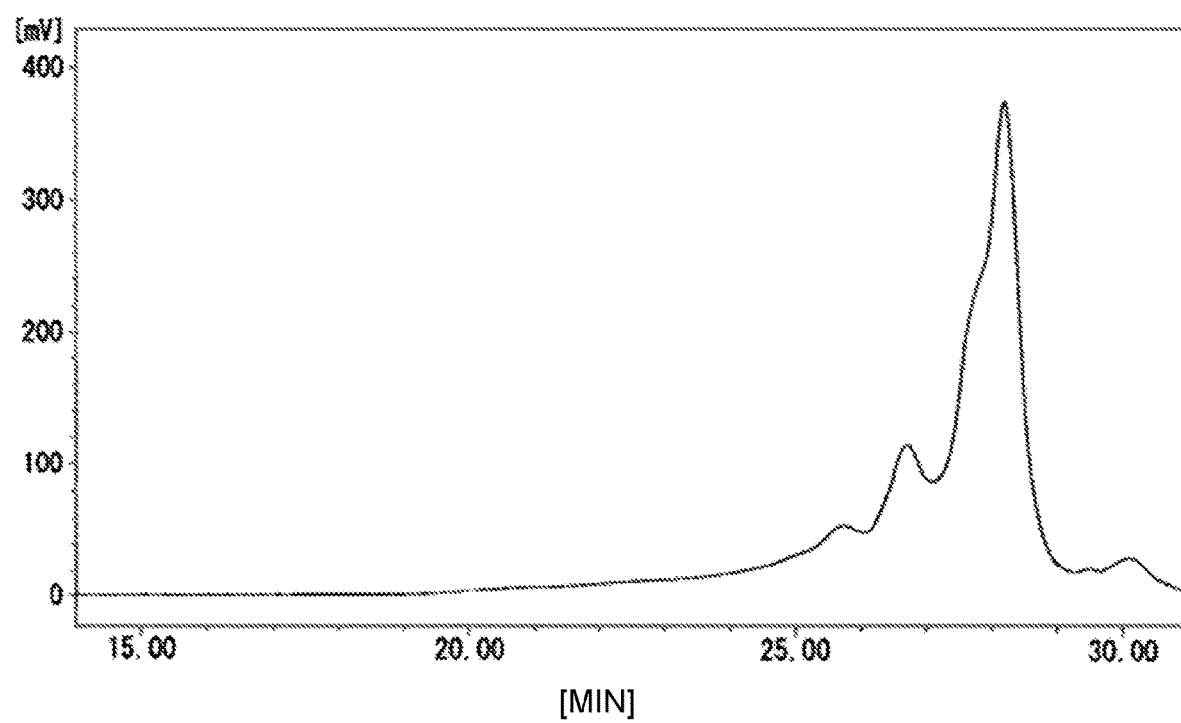
FIG. 3 is an illustration of a GPC chart of a polyfunctional vinyl resin obtained in Example 1.

100 parts of the polyhydric hydroxy resin (P1), 230 parts of diethylene glycol dimethyl ether, and 51.1 parts of chloromethylstyrene were loaded into the same apparatus as that of Synthesis Example 1, and the temperature of the mixture was increased to 70° C. so that the resin was dissolved. 39.5 parts of a 48% aqueous solution of potassium hydroxide was dropped into the solution over 1 hr, and the mixture was subjected to a reaction at 75° C. for 4 hr. The absence of any residual chloromethylstyrene was recognized by gas chromatography, and the solvent was recovered under reduced pressure. The resultant resin was dissolved in 300 parts of toluene, and the solution was washed with 100 parts of water until the pH of its water layer became 7. After that, the solvent was evaporated under reduced pressure. Thus, 203 parts of a vinyl resin (V1) that was a toluene solution having a non-volatile content of 65% was obtained. The resin had a vinyl equivalent of 417 and a total chlorine amount of 1,150 ppm. The GPC chart of the polyfunctional vinyl resin obtained in Example 1 is shown in FIG. 3.

Example 2

100.0 parts of the polyhydric hydroxy resin (P2), 230 parts of diethylene glycol dimethyl ether, and 44.7 parts of chloromethylstyrene were loaded into the same apparatus as that of Synthesis Example 1, and the temperature of the mixture was increased to 70° C. so that the resin was dissolved. 34.6 parts of a 48% aqueous solution of potassium hydroxide was dropped into the solution over 1 hr, and the mixture was subjected to a reaction at 75° C. for 4 hr. The absence of any residual chloromethylstyrene was recognized by gas chromatography, and the solvent was recovered under reduced pressure. The resultant resin was dissolved in 320 parts of toluene, and the solution was washed with 100 parts of water until the pH of its water layer became 7. After that, the solvent was evaporated under reduced pressure. Thus, 196 parts of a vinyl resin (V2) that was a toluene solution having a non-volatile content of 65% was obtained. The resin had a vinyl equivalent of 462 and a total chlorine amount of 1,030 ppm.

Example 3

100 parts of the polyhydric hydroxy resin (P3), 230 parts of diethylene glycol dimethyl ether, and 71.7 parts of chloromethylstyrene were loaded into the same apparatus as that of Synthesis Example 1, and the temperature of the mixture was increased to 70° C. so that the resin was dissolved. 55.4 parts of a 48% aqueous solution of potassium hydroxide was dropped into the solution over 1 hr, and the mixture was subjected to a reaction at 75° C. for 4 hr. The absence of any residual chloromethylstyrene was recognized by gas chromatography, and the solvent was recovered under reduced pressure. The resultant resin was dissolved in 370 parts of toluene, and the solution was washed with 100 parts of water until the pH of its water layer became 7. After that, the solvent was evaporated under reduced pressure. Thus, 234 parts of a vinyl resin (V3) that was a toluene solution having a non-volatile content of 65% was obtained. The resin had a vinyl equivalent of 334 and a total chlorine amount of 1,230 ppm.

Comparative Example 1

118.6 parts of the polyhydric hydroxy resin (P4), 277.1 parts of diethylene glycol dimethyl ether, and 81.2 parts of chloromethylstyrene were loaded into the same apparatus as that of Synthesis Example 1, and the temperature of the mixture was increased to 70° C. so that the resin was dissolved. 62.8 parts of a 48% aqueous solution of potassium hydroxide was dropped into the solution over 1 hr, and the mixture was subjected to a reaction at 75° C. for 4 hr. The absence of any residual chloromethylstyrene was recognized by gas chromatography, and the solvent was recovered under reduced pressure. The resultant resin was dissolved in 410 parts of toluene, and the solution was washed with 100 parts of water until the pH of its water layer became 7. After that, the solvent was evaporated under reduced pressure. Thus, 260 parts of a vinyl resin (HV1) that was a toluene solution having a non-volatile content of 65% was obtained. The resin had a vinyl equivalent of 331 and a total chlorine amount of 1,680 ppm.

Comparative Example 2

95.0 parts of the polyhydric hydroxy resin (P5), 222 parts of diethylene glycol dimethyl ether, and 138.1 parts of chloromethylstyrene were loaded into the same apparatus as that of Synthesis Example 1, and the temperature of the mixture was increased to 70° C. so that the resin was dissolved. 106.8 parts of a 48% aqueous solution of potassium hydroxide was dropped into the solution over 1 hr, and the mixture was subjected to a reaction at 75° C. for 4 hr. The absence of any residual chloromethylstyrene was recognized by gas chromatography, and the solvent was recovered under reduced pressure. The resultant resin was dissolved in 500 parts of toluene, and the solution was washed with 100 parts of water until the pH of its water layer became 7. After that, the solvent was evaporated under reduced pressure. Thus, 302 parts of a vinyl resin (HV2) that was a toluene solution having a non-volatile content of 65% was obtained. The resin had a vinyl equivalent of 235 and a total chlorine amount of 1,830 ppm.

Examples 4 to 7 and Comparative Examples 3 to 5

Materials shown in Table 1 were mixed at a blending ratio shown in Table 1, and were dissolved in a solvent to provide a uniform varnish. The varnish was applied to a PET film, and was dried at 130° C. for 5 min, followed by its peeling from the PET film. Thus, a resin composition was obtained. The resin composition was sandwiched between mirror plates, and was cured under reduced pressure at 130° C. for 15 min, and then at 210° C. for 80 min while a pressure of 2 MPa was applied thereto. Thus, a cured article was obtained. The results of the measurement of the dielectric constant, dielectric loss tangent, thermal conductivity, and Tg of the resultant cured article are shown in Table 1.

|  | Example 4 | Example 5 | Example 6 | Example 7 | Comparative Example 3 | Comparative Example 4 | Comparative Example 5 |
|---|---|---|---|---|---|---|---|
| V1 | 100 | | | | | | |
| V2 | | 100 | | | | | |
| V3 | | | 100 | 50 | | | |
| HV1 | | | | | 100 | | |
| HV2 | | | | 50 | | 100 | |
| HV3 | | | | | | | 100 |
| PO | 0.10 | 0.10 | 0.10 | 0.10 | 0.10 | 0.10 | 0.10 |
| AO | 0.04 | 0.04 | 0.04 | 0.04 | 0.04 | 0.04 | 0.04 |
| Dielectric constant | 2.75 | 2.73 | 2.77 | 2.81 | 2.86 | 2.90 | 2.61 |
| Dielectric loss tangent | 0.0024 | 0.0023 | 0.0028 | 0.0030 | 0.0029 | 0.0051 | 0.0026 |

-continued

| | Example 4 | Example 5 | Example 6 | Example 7 | Comparative Example 3 | Comparative Example 4 | Comparative Example 5 |
|---|---|---|---|---|---|---|---|
| Thermal conductivity (W/m · K) | 0.23 | 0.22 | 0.25 | 0.23 | 0.19 | 0.18 | 0.15 |
| Tg (° C.) | 295 | 288 | 276 | 281 | 265 | 289 | 225 |

In addition, each of the cured articles of Examples 4 to 6, and Comparative Examples 3 and 4 was left to stand in an oven under an air atmosphere at 200° C. for 1 hr, and then the dielectric constant and dielectric loss tangent thereof were measured. The results of the measurement, and the ratio at which the dielectric loss tangent changed after the standing as compared to that before the standing are shown in Table 2.

TABLE 2

| | Example 4 | Example 5 | Example 6 | Comparative Example 3 | Comparative Example 4 |
|---|---|---|---|---|---|
| Dielectric constant | 2.75 | 2.73 | 2.77 | 2.86 | 2.90 |
| Dielectric constant [after 200° C. × 1 Hr] | 2.78 | 2.76 | 2.81 | 2.90 | 2.94 |
| Dielectric loss tangent | 0.0024 | 0.0023 | 0.0028 | 0.0029 | 0.0051 |
| Dielectric loss tangent [after 200° C. × 1 Hr] | 0.0031 | 0.0029 | 0.0036 | 0.0056 | 0.0079 |
| Dielectric loss tangent change ratio (%) | 23 | 28 | 22 | 48 | 35 |

The polyfunctional vinyl resins of Examples showed the following excellent physical properties: the resins had high glass transition temperatures, high thermal conductivities, low dielectric constants, and low dielectric loss tangents as compared to those of Comparative Examples.

INDUSTRIAL APPLICABILITY

The polyfunctional vinyl resin and composition of the present invention are each excellent in dielectric property and thermal conductivity, and hence may be utilized in various applications, such as lamination, molding, and adhesion. In particular, the resin and the composition are useful as electronic materials for high-speed communication devices.

The invention claimed is:

1. A polyfunctional vinyl resin, which is represented by the following general formula (1):

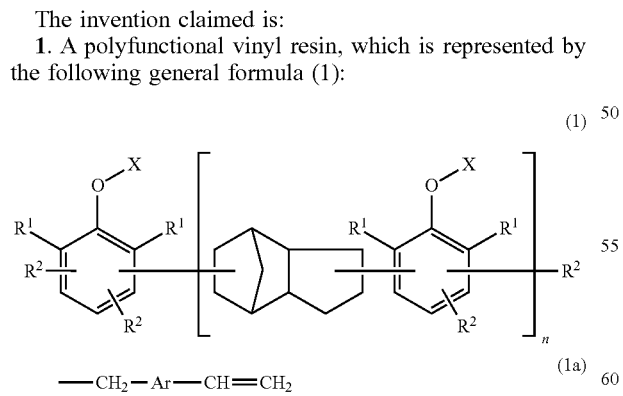

(1)

—CH$_2$—Ar—CH=CH$_2$ (1a)

where

R$^1$s each independently represent a hydrocarbon group having 1 to 8 carbon atoms, R$^2$s each independently represent a hydrogen atom or a dicyclopentenyl group, and at least one thereof represents a dicyclopentenyl group, Xs each independently represent a hydrogen atom or a vinyl group-containing aromatic group represented by formula (1a), and at least one thereof represents a vinyl group-containing aromatic group, and Ar represents an aromatic ring, and "n" represents a number of repetitions, and an average thereof is a number of from 1 to 5.

2. The polyfunctional vinyl resin according to claim 1, wherein Ar in the formula (1a) represents an aromatic ring selected from the group consisting of: a benzene ring; a naphthalene ring; and a biphenyl ring, and the aromatic ring Ar is unsubstituted, or has one or more substituents.

3. A method of producing the polyfunctional vinyl resin of claim 1, comprising:

causing dicyclopentadiene to react at a ratio of from 0.28-fold mol to 2-fold mol with 1 mol of a 2,6-disubstituted phenol represented by the following general formula (2) to provide a polyhydric hydroxy resin represented by the following general formula (3); and then causing the resultant polyhydric hydroxy resin and an aromatic vinylating agent represented by the following general formula (4) to react with each other:

(2)

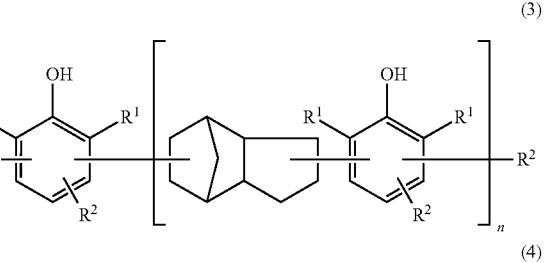

(3)

X—R$^3$ (4)

where
R¹, R², "n", and X are each identical in meaning to the definition in the general formula (1), and
R³ represents a halogen.

4. A polyfunctional vinyl resin composition, comprising, as essential components:
the polyfunctional vinyl resin of claim 1; and
a radical polymerization initiator.

5. A cured article, which is obtained by curing the polyfunctional vinyl resin of claim 1.

6. A prepreg, comprising:
the polyfunctional vinyl resin composition of claim 4 or a semi-cured article thereof; and
a fibrous base material.

7. A resin sheet, comprising:
a resin layer containing the polyfunctional vinyl resin composition of claim 4 or a semi-cured article thereof; and
a supporting film.

8. A laminated plate, which is molded by laminating the prepreg of claim 6.

9. A cured article, which is obtained by curing the polyfunctional vinyl resin composition of claim 4.

10. A laminated plate, which is molded by laminating the resin sheet of claim 7.

11. A laminated plate, which is molded by laminating a prepreg and a resin sheet,
wherein the prepreg comprises:
the polyfunctional vinyl resin composition of claim 4 or a semi-cured article thereof; and
a fibrous base material,
wherein the resin sheet comprises:
a resin layer containing the polyfunctional vinyl resin composition of claim 4 or a semi-cured article thereof; and
a supporting film.

* * * * *